(12) United States Patent
Bertram et al.

(10) Patent No.: US 9,140,803 B2
(45) Date of Patent: Sep. 22, 2015

(54) ACQUISITION PROTOCOL ASSESSMENT APPARATUS

(75) Inventors: Matthias Bertram, Aachen (DE); Jens Wiegert, Aachen (DE); Kevin M. Brown, Mentor on the Lake, OH (US)

(73) Assignee: Koninklijke Philps N.V., Eindhoven (NL)

( * ) Notice: Subject to any disclaimer, the term of this patent is extended or adjusted under 35 U.S.C. 154(b) by 439 days.

(21) Appl. No.: 13/501,257

(22) PCT Filed: Sep. 16, 2010

(86) PCT No.: PCT/IB2010/054194
§ 371 (c)(1),
(2), (4) Date: May 31, 2012

(87) PCT Pub. No.: WO2011/048515
PCT Pub. Date: Apr. 28, 2011

(65) Prior Publication Data
US 2012/0230470 A1    Sep. 13, 2012

Related U.S. Application Data

(60) Provisional application No. 61/253,881, filed on Oct. 22, 2009.

(51) Int. Cl.
*H05G 1/64*    (2006.01)
*G01T 1/02*    (2006.01)
(Continued)

(52) U.S. Cl.
CPC . *G01T 1/02* (2013.01); *A61B 6/032* (2013.01); *A61B 6/544* (2013.01)

(58) Field of Classification Search
CPC ...... A61B 6/032; A61B 6/5258; A61B 6/488; A61B 6/542; A61B 6/544; A61B 6/545; A61B 6/583; G06T 7/0012; G06T 5/002; G06T 2207/10081; G06T 2207/30004; H04N 5/335; H04N 5/357; G01T 1/02
USPC .................. 378/4, 62, 64, 98.5, 165, 210, 901
See application file for complete search history.

(56) References Cited

U.S. PATENT DOCUMENTS 7,813,471 B2   10/2010  Hirokawa et al.
2003/0161548 A1*  8/2003  Vuylsteke .................... 382/274
(Continued)

FOREIGN PATENT DOCUMENTS

EP    1069807 A2    1/2001
EP    1943951 A1    7/2008
(Continued)

OTHER PUBLICATIONS

Shin et al., Isocenter Optimal Matching Shift Algorithm to Verify the Dose Distribution in Intensity-Modulated Radiation Therapy through the Stochastic Property, Nov. 2007, Journal of the Korean Physical Society, vol. 51, No. 5, pp. 1793, 1794, 1797.*

(Continued)

*Primary Examiner* — Irakli Kiknadze
*Assistant Examiner* — Julio M Duarte-Carvajalino (57) ABSTRACT

A method includes generating, via a dose estimator, a dose map indicative of an estimated dose deposited in a subject based on acquisition protocol parameter values of an acquisition protocol of an imaging system, and generating, via a noise estimator, at least one of a noise map indicative of an estimated image noise based on the acquisition protocol parameter values or a contrast-to-noise map based on the noise map and an attenuation map. The method further includes displaying, via a display, the dose and noise maps in a human readable format.

29 Claims, 4 Drawing Sheets

(51) Int. Cl.
*A61B 6/03* (2006.01)
*A61B 6/00* (2006.01)

(56) References Cited

U.S. PATENT DOCUMENTS

2007/0053480 A1    3/2007   Nishide et al.
2007/0147579 A1*   6/2007   De Man et al. ................. 378/16
2008/0037853 A1    2/2008   Bernard et al.
2008/0240336 A1*  10/2008   Miyazaki et al. ................. 378/4

FOREIGN PATENT DOCUMENTS

JP      2005143948 A    6/2005
JP      2008220452 A    9/2008
WO      2011048547 A1   4/2011

OTHER PUBLICATIONS

Goebel et. al., Optimizing the Patient's Dose in Dental Ortho-Pantomographic X-ray by a Bayesian Approach, Utilizing the Scatter-Glare Prior Probability calculated by Monte Carlo Simulations, Apr. 2006, The American Nuclear Society's 14th Biennial Topical Meeting of the Radiation Protection and Shielding Division, p. 11, 14.*

Jannetta, Advanced deconvolution techniques and medical radiography, Oct. 2005, PhD Thesis, University of Northumbria at Newcastle, p. 21, 38, 63.*

Hahn et. al., Numerical comparison of X-ray differential phase contrast and attenuation contrast, Apr. 2012, Biomedical Optics Express, vol. 3, No. 6, p. 1143.* van Zijtveld et al., 3D dose reconstruction for clinical evaluation of IMRT pretreatment verification with an EPID, Feb. 2007, Radiotherapy and Oncology vol. 82, p. 201-207.*

Schwab et al., Comparison of contrast-to-noise ratios of transmission and dark-field signal in grating-based X-ray imaging for healthy murine lung tissue, Sep. 2013, Z. Med. Phys. 23, p. 236-242.*

Berglund et al., Energy weighting improves dose efficiency in clinical practice: implementation on a spectral photoncounting mammography system, Oct.-Dec. 2014, Journal of Medical Imaging vol. 1, No. 3, p. 1-7.*

Goebel et al., Optimizing the Patient's Dose in Dental Ortho-Pantomographic X-ray by a Bayesian Approach, Utilizing the Scatter-Glare Prior Probability calculated by Monte Carlo Simulations, Apr. 3-6, 2006, The American Nuclear Society's 14th Biennial Topical Meeting of the Radiation Protection and Shielding Division, Carlsbad New Mexico, USA.*

Li, X., et al.; Patient-specific dose estimation for pediatric chest CT; 2008; Medical Physics; 35(12)abstract.

Reynaert, N., et al.; Monte Carlo treatment planning for photon and electron beams; 2007; Radiation Physics and Chemistry; 76:643-686.

Wang, J., et al.; Virtual Colonoscopy Screening with Ultra Low-Dose CT and Less-Stressful Bowel Preparation: A Computer Simulation Study; 2008; IEEE Trans. on Nuclear Medicine; 55(5)2566-2575.

McNutt, T.; Dose Calculations: Collapsed Cone Convolution Superposition and Delta Pixel Beam; 2002; Philips Pinnacle 3 White Paper; 4 pages.

* cited by examiner

ACQUISITION PROTOCOL ASSESSMENT APPARATUS

CROSS REFERENCE TO RELATED APPLICATIONS

This application claims the benefit of U.S. provisional application Ser. No. 61/253,881 filed Oct. 22, 2009, which is incorporated herein by reference.

The following generally relates to an acquisition protocol assessment apparatus and is described with particular application to computed tomography (CT). However, it also amenable to other medical imaging applications and to non-medical imaging applications.

A computed tomography (CT) scanner includes an x-ray tube mounted on a rotatable gantry that rotates around an examination region about a longitudinal or z-axis. The x-ray tube emits ionizing radiation that traverses the examination region and irradiates a patient therein. A detector array subtends an angular arc opposite the examination region from the x-ray tube. The detector array detects radiation that traverses the examination region and generates projection data indicative thereof. A reconstructor processes the projection data and reconstructs volumetric image data indicative thereof. The volumetric image data is processed to generate one or more images of the patient.

As noted above, the x-ray tube emits ionizing radiation that irradiates the patient. The radiation dose deposited in the patient is based on various acquisition protocol parameters such as tube current (mAs), tube voltage (kVp), pitch/exposure time (for helical scans), slice thickness and spacing (for axial scans), as well as patient size. Radiation dose can be reduced by decreasing tube current and tube voltage and/or increasing pitch, slice thickness and slice spacing. However, image noise is inversely proportional to radiation dose and, thus, reducing radiation dose increases noise, which reduces image quality.

In one proposed CT system, a noise threshold is pre-set and the system automatically determines a single best set of acquisition protocol parameter values that is optimized to reduce radiation dose while maintaining the pre-set noise threshold. Unfortunately, this is a rigid approach that is done in the background by a computer processor. As a result, in one instance the CT scanner may not be capable of operating under the automatically determined optimized acquisition protocol parameter values. For example, the computer implemented algorithm may not take into account a scanning system limitation (e.g., available kVp, mAs, etc. settings) of the CT system. Furthermore, such an approach does not consider the imaging procedure and thus different acquisition protocol parameter values may be better suited for the particular imaging procedure and/or patient. This may be a judgment call by the radiologist based on years of experience. Moreover, a radiologist may desire to use acquisition protocol parameter values that he/she is familiar with, for example, acquisition protocol parameter values based on dose estimates (CTDI), manufacturer recommendations, or facility determined acquisition protocol parameter values.

Aspects of the present application address the above-referenced matters and others.

According to one aspect, a method includes generating, via a dose estimator, a dose map indicative of an estimated dose deposited for a subject based on acquisition protocol parameter values of an acquisition protocol of an imaging system, and generating, via a noise estimator, at least one of a noise map indicative of an estimated image noise based on the acquisition protocol parameter values or a contrast-to-noise map based on the noise map and an attenuation map. The method further includes displaying, via a display, the dose and noise maps in a human readable format.

In another embodiment, an acquisition protocol assessment apparatus include a dose estimator, a noise estimator and an analysis component. The dose estimator generates a dose map indicative of an estimated dose deposited for a subject based on parameter values of an acquisition protocol of an imaging system. The noise estimator generates a noise map indicative of an estimated image noise for the subject based on the parameter values. The analysis component displays, via a display, the dose and noise maps in a human readable format.

In another embodiment, a method includes identifying at least two different acquisition protocols of the imaging system. The method further includes generating first and second dose maps respectively for the at least two acquisition protocols based on corresponding parameter values of the protocols and at least one of first and second noise maps or first and second contrast-to-noise maps respectively for the at least two acquisition protocols based on the corresponding parameter values of the protocols. The method further includes concurrently displaying the first and second dose maps and at least one of the first and second noise maps or the first and second contrast-to-noise maps in a human readable format.

In another embodiment, a method includes generating a first dose map for a first acquisition protocol of the imaging system, a first noise map for the first acquisition protocol, an attenuation map based on available kVp values, and a first contrast-to-noise map based on the first noise map and the attenuation map. The method further includes identifying protocol parameter optimization criteria, wherein the criteria identifies one or more of a contrast medium of interest, an energy range of interest, and an imaging task of interest. The method further includes generating the set of protocol parameter values for the data acquisition protocol, optimized based on the optimization criteria and one or more of the dose map, the noise map, the contrast-to-noise map, and the attenuation map.

In another embodiment, a method includes generating at least one of a difference dose map, a difference noise map or a difference contrast-to-noise map respectively based on the first and second dose maps, the first and second noise maps or the first and second contrast-to-noise maps, and displaying at least one of the generated difference maps.

The invention may take form in various components and arrangements of components, and in various steps and arrangements of steps. The drawings are only for purposes of illustrating the preferred embodiments and are not to be construed as limiting the invention.

Figure 1:
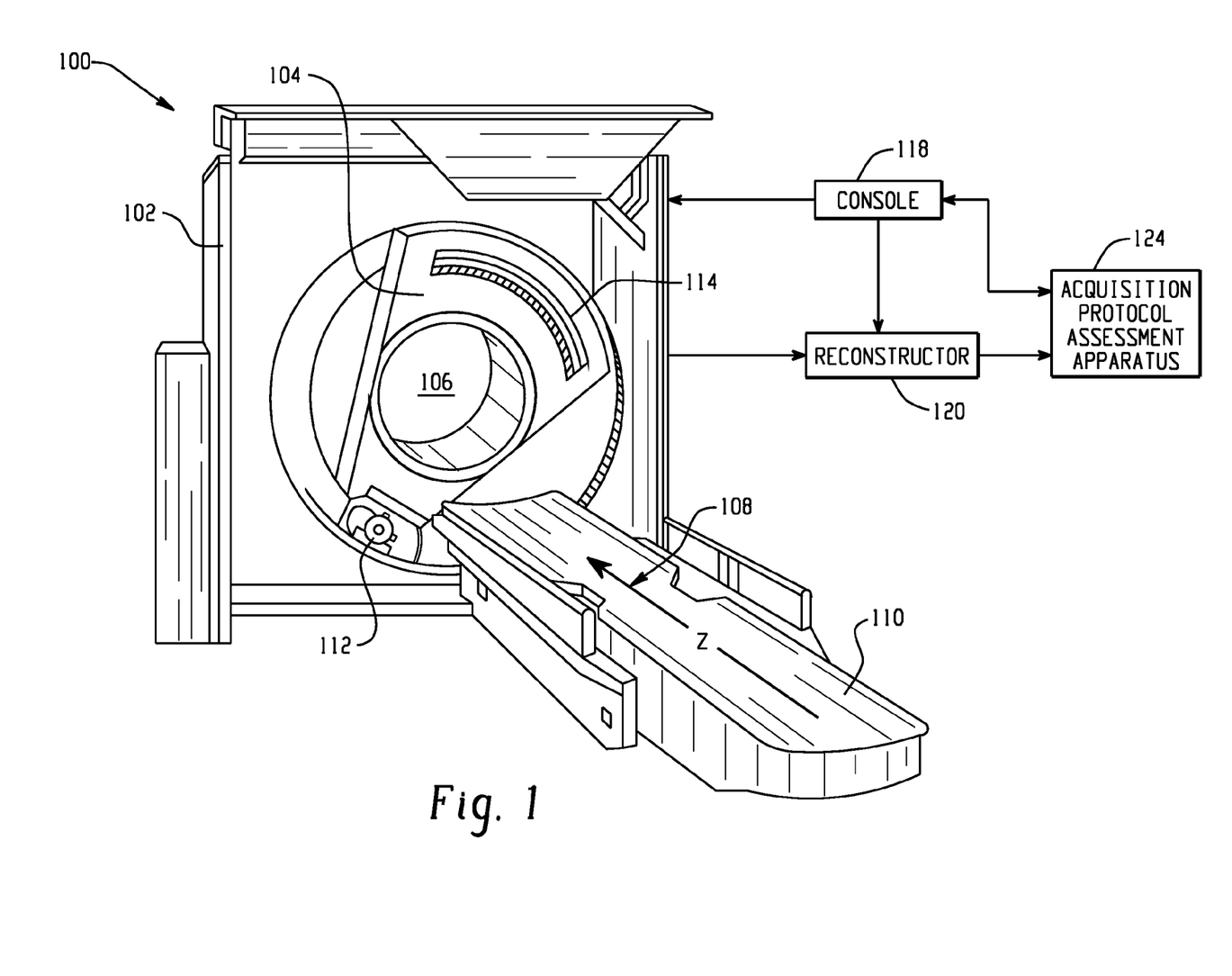
FIG. 1 illustrates an example imaging system in connection with an image data assessment apparatus.

FIG. 1 illustrates an imaging system 100 such as a computed tomography (CT) scanner. The imaging system 100 includes a generally stationary gantry 102 and a rotating gantry 104. The rotating gantry 104 is rotatably supported by the stationary gantry 102 and rotates around an examination region 106 about a longitudinal or z-axis 108. A patient support 110, such as a couch, supports an object or subject such as a human patient in the examination region 106.

A radiation source 112, such as an x-ray tube, is supported by the rotating gantry 104. The radiation source 112 emits ionizing radiation from a focal spot and the radiation traverses the examination region 106 and an object or subject therein. A source collimator collimates the radiation to form a generally cone, wedge, fan or other shaped radiation beam.

A two-dimensional radiation sensitive detector array 114 subtends an angular arc opposite the radiation source 112 across the examination region 106. The detector array 114 includes a plurality of rows of detectors that extend along the z-axis direction. The detector array 114 detects radiation traversing the examination region 106 and generates projection data indicative thereof.

A general-purpose computing system or computer serves as an operator console 118. A processor of the console 118 executes computer readable instructions on the console 118, which allows the operator to control operation of the system 100 such as selecting acquisition protocol (e.g., diagnostic, 3D low dose non-diagnostic, etc.), setting scan protocol parameters values, initiating scanning, etc.

A reconstructor 120 reconstructs the projection data and generates three-dimensional (3D) volumetric image data indicative thereof. The volumetric image data can be processed to generate one or more images of the object or subject.

An acquisition protocol assessment apparatus 124 assesses acquisition protocol parameter values. As described in greater detail below, the acquisition protocol assessment apparatus 124 estimates deposited dose for a subject for one or more acquisition protocols, determines dose, image noise and/or contrast-to-noise profiles or maps for one or more acquisition protocols, and/or determines acquisition protocol parameter values based on optimization criteria and/or scan parameter policies.

In one instance, this allows a clinician to estimate the dose for a subject based on the protocol used to scan the subject and the image data from the scan. In another instance, this allows the clinician to estimate dose for a plurality of protocols available to the system 100. This information could be used to compare dose between two or more acquisition protocols, retrospectively and/or prospectively. In yet another instance, this allows the clinician to tune the protocol parameters based on optimization criteria such as dose, noise, contrast of a material of interest, an objective of the imaging procedure, etc.

In the illustrated embodiment, the acquisition protocol assessment apparatus 124 is part of the system 100, but separate from the console 118. In another embodiment, the acquisition protocol assessment apparatus 124 is part of the console 118. In yet another embodiment, the acquisition protocol assessment apparatus 124 is located remote from the system 100, for example, in a workstation outside of the exam room in which the system 100 is located.

The acquisition protocol assessment apparatus 124 may include one or more processors and computer readable storage medium that stores computer executable instructions, executable by the one or more processors. In one non-limiting instance, the one or more processors execute the instructions to implement one or more of the below described components of the acquisition protocol assessment apparatus 124.

Figure 2:
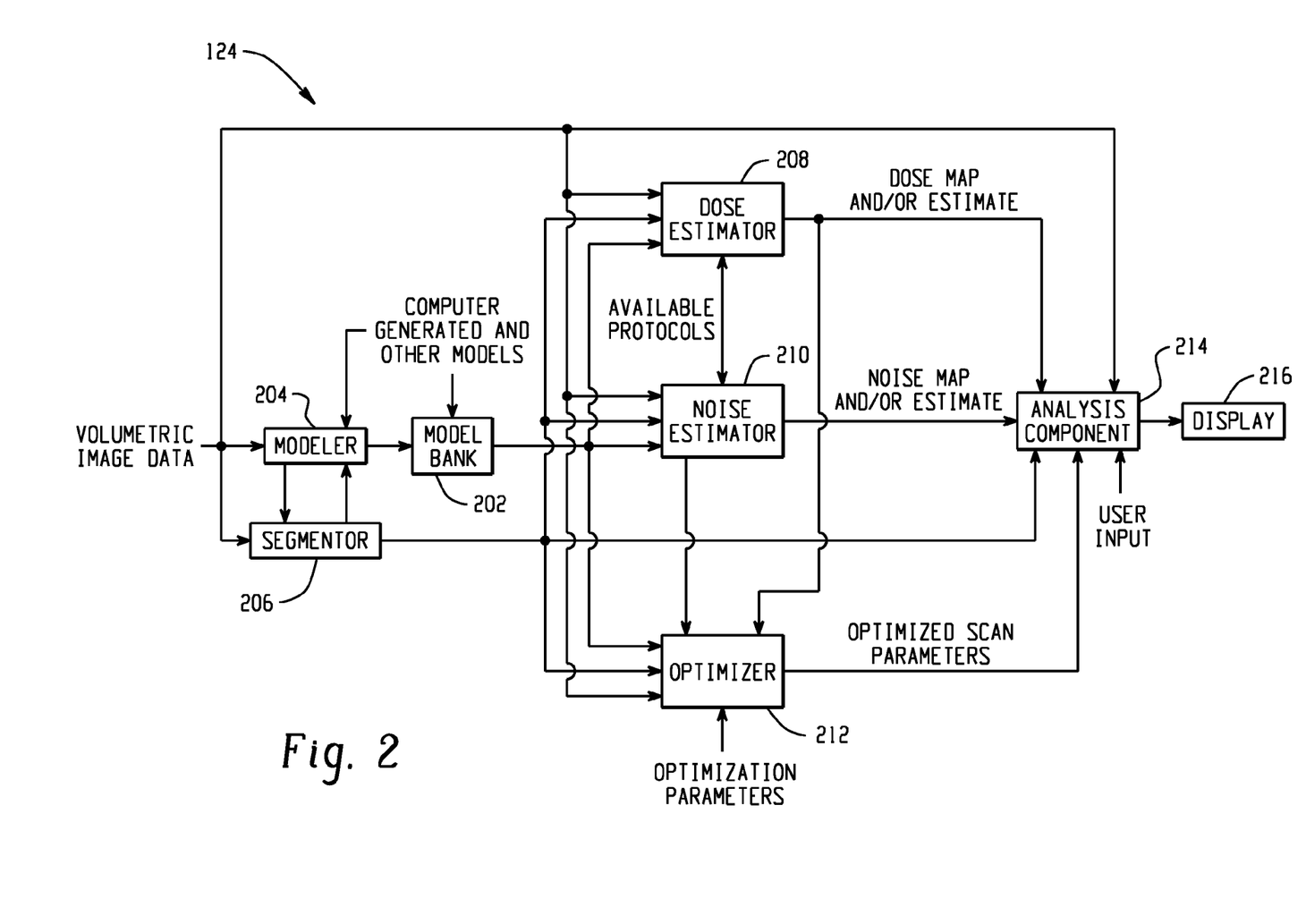
FIG. 2 illustrates an example image data assessment apparatus.

FIG. 2 illustrates an example of the acquisition protocol assessment apparatus 124.

A model bank 202 stores anatomical models, including models that can be used to estimated dose and/or image noise, determine dose and/or image noise profiles, and/or generate optimized acquisition protocol parameter values. As shown, the model bank 202 may store computer-generated anatomical models. Such models include mesh, vector graphics, finite element analysis, and/or other based models, including graphical and/or equation based models.

A modeler 204 generates anatomical models based on volumetric image data such as volumetric image data reconstructed by the reconstructor 120 of the system 100 (FIG. 1). Likewise, these models can be mesh, vector graphics, finite element analysis, and/or otherwise based, and stored in the model bank 202. This illustrated modeler 204 can additionally use the computer-generated models, for example, to fit a representation of anatomical structure in an anatomical model to the corresponding anatomy in the volumetric image data and/or vice versa.

A segmentor 206 can be used to segment the volumetric image data based on anatomy of interest (e.g. bone, air, tissue, etc.), material or medium of interest (e.g., contrast medium, etc.), and/or otherwise. The modeler 204 can generate anatomical and/or material specific models based on the segmented data. These models can also be stored in the model bank 202.

A dose estimator 208 estimates deposited radiation dose for a region of interest and generates dose distribution maps, which includes information indicative of a spatial distribution of the deposited dose for particular anatomy, based thereon. The illustrated dose estimator 208 is configured to estimate dose based on one or more acquisition protocol parameter values (e.g., kVp, mAs, etc.) for one or more acquisition protocols.

In one instance, the dose estimator 208 estimates dose based on the acquisition protocol parameter values used to scan the subject and the volumetric image data generated from the scan. The estimated dose can be used to estimate the dose deposited for the imaging procedure, particular anatomy of the subject (e.g., organ specific), a lifetime accumulated dose, and/or other information. Additionally or alternatively, the estimated dose can be used to predict dose for another subject with similar physical characteristics (e.g., height, weight, etc.), pathologies, etc., prior to the other subject being scanned.

The volumetric image data may be from a diagnostic scan or a pre-scan such as a 3D low dose or other pre-scan. Where the volumetric image data is from a diagnostic scan, the estimated dose can also be used to facilitate planning a follow up scan of the subject or another subject with similar physical characteristics. Where the volumetric image data is from a pre-scan, the estimated dose can be used to facilitate planning the diagnostic scan. In another instance, a model from the model bank 202 is used instead of the volumetric image data. A scout/pilot scan and/or other data can be used to facilitate estimating dose based on a model.

The dose estimator 208 is also configured to estimate dose based on the parameter values of one or more acquisition protocols of the system 100, again, along with either volumetric image data or a model. The estimated dose can be used to compare the expected deposited dose for the one or more acquisition protocols. This allows a clinician to validate the acquisition protocol selected to scan the subject and/or select an acquisition protocol based on dose characteristics of interest. Similarly, the estimated dose can be used to predict dose for a future scan of one or more subjects.

The dose estimator 208 can use various algorithms to estimate dose and generate dose maps. Examples of suitable algorithms used to generate dose maps include, but are not limited to, a Monte-Carlo algorithm, a fast dose algorithm such as the fast dose algorithm described in McNutt, T., "Dose Calculations: Collapsed Cone Convolution Superposition and Delta Pixel Beam," Pinnacle White Paper Nr. 4535 983 02474 Philips 2002, and/or other algorithm.

A noise estimator 210 estimates image noise for a region of interest and generates noise distribution profiles or maps based thereon. The noise estimator 210 also generates contrast-to-noise maps based on the noise maps and one or more attenuation maps. This includes estimating noise for higher dose acquisitions based on lower dose acquisitions and vice versa. The noise estimator 210 can employ various algorithms to estimate noise, including a noise propagation model that allows for spatially resolved computation of noise in reconstructed images based on noise distributions. An example of a suitable noise propagation model is described in international patent application PCT/IB2009/052686, filed Jun. 23, 2009, which is incorporated in its entirety herein by reference.

Similar to the dose estimator 208, the noise estimator 210 can estimate noise based on acquisition protocol parameters values used to scan a subject and/or acquisition protocol parameters values available for use by the imaging system 100. In addition, the noise estimator 210 can estimate noise based on volumetric image data (including segmented image data) corresponding to the subject or another subject and/or one or more anatomical models in the model bank 202.

An optimizer 212 determines a set of optimized acquisition protocol parameters values (e.g. kVp, wedge type, optimal dose modulation, total mA required to reach a predefined noise level in a ROI). The illustrated parameter optimizer 212 generates the optimized set of acquisition protocol parameters values based on optimization criteria and either volumetric image data or a model. The parameter optimizer 212 also uses one or more dose maps, noise maps, contrast-to-noise maps, and/or simulated attenuation maps to determine the optimized parameter values.

Where the optimizer 212 is programmed so that it can recommend a kVp value for a protocol, the optimizer 212 uses a dose map and an attenuation map that can be employed to determine the actual contrast between the different structures, which may change based on the kVp, in an image. Examples of suitable optimization criteria include, but are not limited to, as a predetermined noise threshold or range, radiation dose threshold or range, a combination thereof, a particular objective or task of the imaging procedure, image contrast between different materials used during the imaging procedure, contrast-to-noise ratio, and/or other criteria.

By way of example, suitable task optimization criteria may indicate that the optimizer 212 should generate a set of acquisition protocol parameter values based on tissue of interest (e.g., bone, soft tissue, etc.), energy(s) of interest, system configuration (single or multi tube, single or multi layer detectors, etc.), etc. Suitable material-specific optimization criteria may indicate that the optimizer 212 should generate a set of acquisition protocol parameter values based on a contrast medium, a calcification, a tumor, etc.

The optimizer 212 can take such criteria into account when generating the optimized acquisition protocol parameter values and/or after generating the acquisition protocol parameter values in which the optimizer 212 determines a modification to the acquisition protocol parameter values, which optimizes the acquisition protocol parameter values for the task and/or material.

For spectral imaging applications, optimized acquisition protocol parameter values for one or more of the energy ranges or bins (e.g., photo-electric, Compton, k-edge(s), etc.) can be individually determined, and then the individually optimized values can be combined to generate a set of optimized parameter values for the imaging procedure. The values for the individual energy ranges can be variously weighted to emphasize or suppress one or more of the energy ranges.

For interventional imaging applications, example optimization criteria may be to reduce dose to the interventionalist. The optimization may be based on an expected location of the interventionalist performing the procedure, including where his/her arms and hands will be during the procedure. In another instance, a camera or other device, which generates a signal that can be used to determine the location of the interventionalist, is used to provide adaptive feedback indicative of the location of the interventionalist.

An analysis component 214 analyzes one or more of the volumetric image data, segmented volumetric image data, a model of anatomy, a dose estimate, a dose map, a noise estimate, a noise map, a contrast-to-noise ratio, a contrast-to-noise map, optimized data acquisition parameter values, and/or other information, individually or in combination.

The illustrated analysis component 214 is also configured to accept a user input. Suitable input includes acquisition protocol parameter values, changes to acquisition protocol parameter values, select of one or more particular acquisition protocols, etc. This allows a clinician to identify an acquisition protocol based on dose, noise, a combination of dose and noise, and/or other features.

A presentation component 216 presents one or more of the volumetric image data, segmented volumetric image data, a dose estimate, a dose map, a noise estimate, a noise map, a contrast-to-noise ratio, a contrast-to-noise map, optimized data acquisition parameter values, and/or other information, individually or in combination. The presentation component 216 can present such information via a graphical user or other interface of a display or monitor.

The displayed information allows a clinician to visually inspect and compare the affect of various acquisition protocol parameter values on noise and/or dose. For instance, for one or more protocols, a pre-defined total (or organ) dose can be assumed, and the corresponding noise maps can be compared. Alternatively, for one or more protocols, a pre-defined noise range for a predetermined region of interest (ROI) is assumed, and the corresponding dose maps are scaled accordingly and can be compared.

Figure 3:
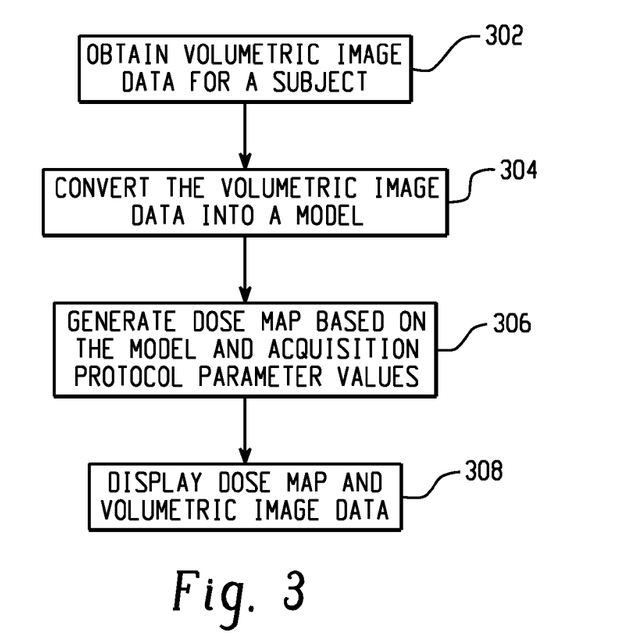
FIGS. 3-6 illustrate example methods.

FIG. 3 illustrates a method for determining dose deposited for a subject based on an imaging procedure.

At 302, volumetric image data generated based on the imaging procedure is obtained. As discussed herein, the volumetric image data may correspond to a diagnostic scan or a pre-scan used to plan a diagnostic scan.

At 304, the volumetric image data is converted into a model. Alternatively, a suitable computer generated anatomical model is obtained.

At 306, a dose map is generated based on the model and the acquisition protocol parameter values used during the imaging procedure.

At 308, the dose map and the volumetric image data are displayed. The dose map and the volumetric image data can be displayed individually or concurrently (e.g., superimposed, side-by-side, etc.).

Figure 4:
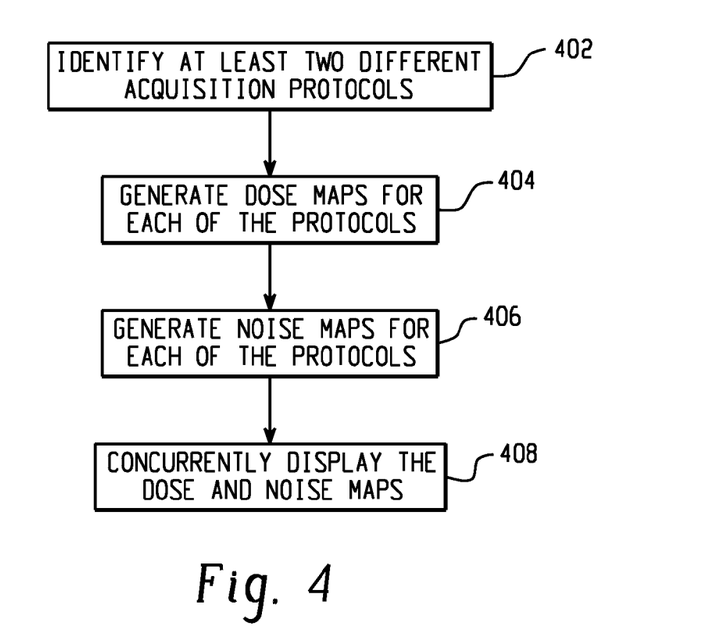

FIG. 4 illustrates a method for determining dose and/or noise characteristics for alternative data acquisition protocols of the imaging system 100.

At 402, at least two different acquisition protocols of the imaging system 100 are identified.

At 404, first and second dose maps are respectively generated for the at least two acquisition protocols based on corresponding parameter values of the protocols and volumetric image data or at least one anatomical model.

At 406, first and second noise maps are respectively generated for the at least two acquisition protocols based on the corresponding parameter values of the protocols and the volumetric image data or the at least one anatomical model.

At 408, the first and second dose maps and the first and second noise maps are concurrently displayed in a human readable format. The first and second dose maps can also be used to generate a difference dose map, which can additionally or alternatively be displayed.

First and second contrast-to-noise maps and/or contrast-to-noise difference maps can also be generated and displayed, individually or concurrently with one or more of the dose or noise maps. As discussed herein, contrast-to-noise maps can be generated based on noise and attenuation maps.

Figure 5:
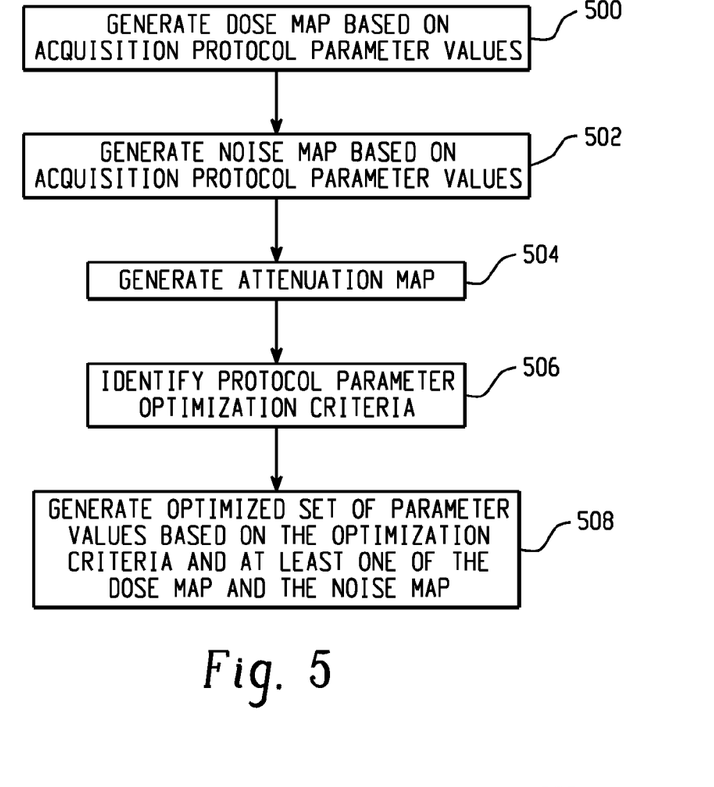

FIG. 5 illustrates a method for generating a set of optimized data acquisition protocol parameter values.

At 500, a dose map is generated for at least one acquisition protocol of the imaging system 100.

At 502, a noise map is generated for the at least one acquisition protocol.

At 504, an attenuation map is generated. As note herein, the attenuation map indicates actual contrast of structures in an image as a function of kVp.

At 506, protocol parameter optimization criteria is identified. As discussed herein, the criteria may be based on one or more of dose, noise, task, material, contrast-to-noise ratio, etc.

At 508, a set of protocol parameter values is generated for the data acquisition protocol, optimized based on one or more of the dose map, the noise map, the attenuation map, and the parameter optimization criteria.

Figure 6:
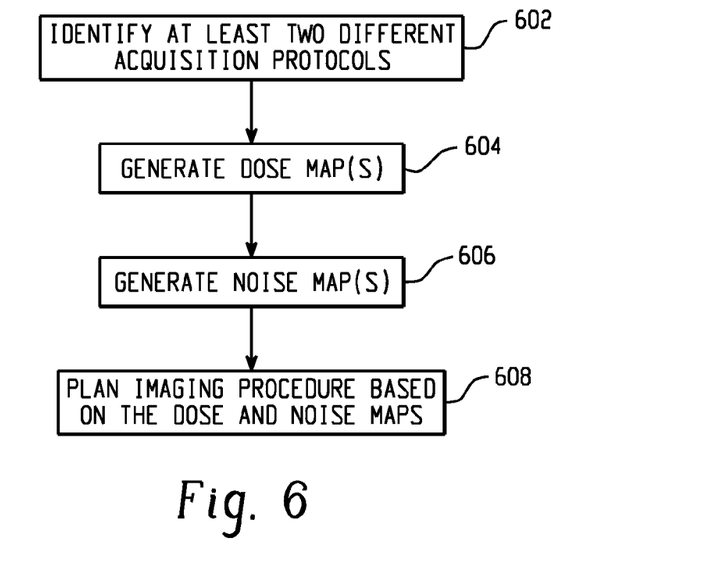

FIG. 6 illustrates a method for estimating dose for a subject to be scanned based on one or more available acquisition protocols.

At 602, one or more of volumetric image data from a previous scan of the subject, volumetric image data for a different subject, or an anatomical model is obtained.

At 604, one or more dose maps are generated based on one or more of the volumetric image data from a previous scan of the subject, the volumetric image data for the different subject, or the anatomical model.

At 606, one or more noise maps are generated based on one or more of the volumetric image data from a previous scan of the subject, the volumetric image data for the different subject, or the anatomical model.

At 608, an imaging procedure is planned for a subject based on the dose map and the noise map.

First and second contrast-to-noise maps can also be generated as discussed herein and displayed, individually or concurrently with one or more of the dose or noise maps, and the planning of the imaging procedure (act 608) can additionally or alternatively be based on the contrast-to-noise maps.

In another embodiment, scan parameter protocol compliance with a scan parameter policy can additional be presented along with one or more of the dose, image noise, attenuation, and/or contrast-to-noise maps for one or more scan protocols. An example of generating and employing a scan parameter policy to determine compliance is described in connection with provisional patent application Ser. No. 61/253,880, filed on Oct. 22, 2009, and entitled "Scan Parameter Policy," the entirety of which is incorporated herein by reference.

The above may be implemented by way of computer readable instructions, which, when executed by a computer processor(s), causes the processor(s) to carry out the acts described herein. In such a case, the instructions are stored in a computer readable storage medium such as memory associated with and/or otherwise accessible to the relevant computer.

The invention has been described herein with reference to the various embodiments. Modifications and alterations may occur to others upon reading the description herein. It is intended that the invention be construed as including all such modifications and alterations insofar as they come within the scope of the appended claims or the equivalents thereof.

What is claimed is:

1. A method, comprising:
    generating, via a dose estimator, a dose map indicative of an estimated X-ray radiation dose deposited in a subject based on acquisition protocol parameter values of an acquisition protocol of an imaging system, and the dose map includes a plurality of dose values indicative of spatially distributed dose; and
    generating, via a noise estimator, a contrast-to-noise map based on a noise map and an attenuation map, wherein the noise map is indicative of an estimated image noise based on the acquisition protocol parameter values, and the contrast-to-noise map includes a plurality of contrast-to-noise values indicative of spatially distributed contrast-to-noise, and the noise map includes a plurality of noise values indicative of spatially distributed noise, and the attenuation map includes a plurality of attenuation values indicative of spatially distributed attenuation; and
    displaying, via a display, the dose map and the contrast-to-noise map in a human readable format.

2. The method of claim 1, wherein the acquisition protocol is an acquisition protocol used to scan the subject with the imaging system.

3. The method of claim 1, wherein the acquisition protocol includes one of a set of acquisition protocols of the imaging system selectable for scanning the subject.

4. The method of claim 1, further comprising:
    generating two or more dose maps for two or more acquisition protocols of the imaging system, and each of the two or more dose maps includes a plurality of dose values indicative of spatially distributed dose;
    generating at least one of two or more noise maps or two or more contrast-to-noise maps for the two or more acquisition protocols, and each of the two or more contrast-to-noise maps includes a plurality of contrast-to-noise values indicative of spatially distributed contrast-to-noise, and each of the two or more noise maps includes a plurality of noise values indicative of spatially distributed noise; and
    concurrently displaying the dose maps and at least one of the noise maps or the contrast-to-noise maps.

5. The method of claim 1, further comprising: receiving an input indicative of a change to at least one parameter value of the acquisition protocol, and generating and displaying a dose map and a noise map based on the change, and the generated and displayed noise map includes a plurality of noise values indicative of spatially distributed noise, and the generated and displayed dose map includes a plurality of dose values indicative of spatially distributed dose.

6. The method of claim 1, further comprising: generating at least one of the dose and noise maps based on volumetric image data.

7. The method of claim 6, wherein the volumetric image data corresponds to image data for the subject generated based on data acquired using the acquisition protocol.

8. The method of claim 6, wherein the volumetric image data corresponds to image data acquired for a different subject.

9. The method of claim 1, further comprising: generating at least one of the dose and noise maps based on an anatomical model.

10. The method of claim 1, further comprising:
    determining a set of acquisition parameter values based on at least one of the dose map, the contrast-to-noise map, and the noise map, and optimization criteria.

11. The method of claim 10, wherein the optimization criteria is based on a radiation energy range of interest.

12. The method of claim 10, wherein the optimization criteria is based on contrast of a medium of interest.

13. The method of claim 10, wherein the optimization criteria is based on an imaging task of interest.

14. The method of claim 10, wherein the optimization criteria is a radiation dose threshold, an image noise threshold, a threshold of a contrast-to-noise ratio, or a combination thereof.

15. The method of claim 1, further including:
receiving user input indicative of a change to at least one parameter value of the acquisition protocol, and generating and displaying a second dose map and a second contrast-to-noise map based on the change, and the second contrast-to-noise map includes a plurality of contrast-to-noise values indicative of spatially distributed contrast-to-noise, and the second dose map includes a plurality of dose values indicative of spatially distributed dose.

16. An acquisition protocol assessment apparatus, comprising:
a dose estimator that generates a dose map indicative of an estimated X-ray radiation dose deposited in a subject based on parameter values of an acquisition protocol of an imaging system, and the dose map includes a plurality of dose values indicative of spatially distributed dose; and
a noise estimator that generates a contrast-to-noise map based on a noise map and an attenuation map, wherein the noise map is indicative of an estimated image noise for the subject based on the parameter values, and the contrast-to-noise map includes a plurality of contrast-to-noise values indicative of spatially distributed contrast-to-noise, and the noise map includes a plurality of noise values indicative of spatially distributed noise, and the attenuation map includes a plurality of attenuation values indicative of spatially distributed attenuation; and
an analysis component that displays, via a display, the dose and noise maps in a human readable format.

17. The acquisition protocol assessment apparatus of claim 16, wherein the noise estimator generates a contrast-to-noise map based on the noise map and an attenuation map, and the dose and noise maps are further generated based on one or more of volumetric image data corresponding to the subject, volumetric image data corresponding to a different subject, or an anatomical model.

18. The acquisition protocol assessment apparatus of claim 16, wherein the acquisition protocol includes one or more of a protocol used to scan the subject, a protocol used to scan a different subject, or at least two protocols of the imaging system.

19. The acquisition protocol assessment apparatus of claim 16, further comprising:
an optimizer that determines a set of acquisition parameter values based on at least one of a contrast medium of interest, an energy of interest, and an imaging objective of interest.

20. The acquisition protocol assessment apparatus of claim 16, wherein the analysis component concurrently displays dose and noise maps for one or more different acquisition protocols.

21. The acquisition protocol assessment apparatus of claim 16, wherein the analysis component displays at least one of a differential dose map, a differential noise map or a differential contrast-to-noise map respectively indicative of a difference between two dose maps, two noise maps or two contrast-to-noise maps for different acquisition protocols, and each of the two contrast-to-noise maps includes a plurality of contrast-to-noise values indicative of spatially distributed contrast-to-noise, and each of the two noise maps includes a plurality of noise values indicative of spatially distributed noise, and each of the two dose maps includes a plurality of dose values indicative of spatially distributed dose.

22. A method for identifying X-ray radiation dose and/or noise profiles for alternative data acquisition protocols of an imaging system, comprising:
identifying at least two different acquisition protocols of the X-ray imaging system;
generating first and second dose maps respectively for the at least two acquisition protocols based on corresponding parameter values of the protocols, and the first and second dose maps each include a plurality of dose values indicative of spatially distributed dose;
generating first and second contrast-to-noise maps respectively for the at least two acquisition protocols based on the corresponding parameter values of the protocols, and the contrast-to-noise maps include a plurality of contrast-to-noise values indicative of spatially distributed contrast-to-noise; and
concurrently displaying first and second dose maps and at least one of the first and second contrast-to-noise maps or the first and second contrast-to-noise maps in a human readable format.

23. The method of claim 22, further comprising: optimizing a set of acquisition protocol parameter values based on one or more of the dose maps and the contrast-to-noise maps, an attenuation map, and optimization criteria, and the attenuation map includes a plurality of attenuation values indicative of spatially distributed attenuation.

24. The method of claim 22, further comprising: optimizing a set of acquisition protocol parameter values based on one or more of a contrast medium of interest, an energy range of interest, or an imaging task of interest.

25. The method of claim 22, further comprising: generating at least one of the dose or noise maps based on one or more of volumetric image data corresponding to a subject, volumetric image data corresponding to a different subject, or an anatomical model.

26. A method for generating a set of optimized data acquisition protocol parameter values based on optimization criteria, comprising:
generating a first X-ray radiation dose map for a first acquisition protocol of an imaging system, and the first X-ray radiation dose map includes a plurality of dose values indicative of spatially distributed dose;
generating a first noise map for the first acquisition protocol, and the noise map includes a plurality of noise values indicative of spatially distributed noise;
generating an attenuation map based on available kVp values, and the attenuation map includes a plurality of attenuation values indicative of spatially distributed attenuation;
generating a first contrast-to-noise map based on the first noise map and the attenuation map, and the contrast-to-noise map includes a plurality of contrast-to-noise values indicative of spatially distributed contrast-to-noise;
identifying protocol parameter optimization criteria, wherein the protocol parameter criteria identifies one or more of a contrast medium of interest, an energy range of interest, and an imaging task of interest; and
generating the set of protocol parameter values for the data acquisition protocol, optimized based on the optimization criteria and one or more of the X-ray radiation dose map, the noise map, the contrast-to-noise map, and the attenuation map.

27. The method of claim 26, comprising:

generating a second X-ray radiation dose map for a second acquisition protocol of the imaging system, and the second X-ray radiation dose map includes a plurality of dose values indicative of spatially distributed dose;

generating a second noise map for the second acquisition protocol, and the second noise map includes a plurality of noise values indicative of spatially distributed noise;

generating a second contrast-to-noise map for the second acquisition protocol, and the second contrast-to-noise map includes a plurality of contrast-to-noise values indicative of spatially distributed contrast-to-noise; and concurrently displaying the first and second X-ray radiation dose maps and at least one of the first and second noise maps or the first and second contrast-to-noise maps in a human readable format.

28. The method of claim 27, further comprising:

generating at least one of a difference dose map, a difference noise map or a difference contrast-to-noise map respectively based on the first and second X-ray radiation dose maps, the first and second noise maps or the first and second contrast-to-noise maps; and displaying at least one of the generated difference maps.

29. The method of claim 26, further comprising:

generating at least one of the X-ray radiation dose or noise maps based on one or more of volumetric image data corresponding to a subject, volumetric image data corresponding to a different subject, or an anatomical model.

\* \* \* \* \*